(12) United States Patent
Rimlinger et al.

(10) Patent No.: US 7,488,307 B2
(45) Date of Patent: Feb. 10, 2009

(54) SECURITY ASSEMBLY FOR FITTING TO A SYRINGE, AND A SYRINGE ASSEMBLY

(75) Inventors: Thierry Rimlinger, L'isle D'Abeau (FR); Guillaume Belle, Vinay (FR); Pascal Dugand, Estrablin (FR)

(73) Assignee: Rexam Pharma la Verpilliere, La Verpilliere Dedex (FR)

( * ) Notice: Subject to any disclaimer, the term of this patent is extended or adjusted under 35 U.S.C. 154(b) by 383 days.

(21) Appl. No.: 10/987,177

(22) Filed: Nov. 12, 2004

(65) Prior Publication Data

US 2005/0148932 A1 Jul. 7, 2005

(51) Int. Cl.
*A61M 5/32* (2006.01)
*A61M 5/00* (2006.01)

(52) U.S. Cl. .................. 604/197; 604/110; 604/263; 604/272; 128/919

(58) Field of Classification Search ............... 604/110, 604/111, 187–200, 218, 263, 272; 128/919
See application file for complete search history.

(56) References Cited

U.S. PATENT DOCUMENTS

| 3,895,633 | A | * | 7/1975 | Bartner et al. ............ 604/192 |
| 5,338,310 | A | * | 8/1994 | Lewandowski ........... 604/192 |
| 6,186,980 | B1 | * | 2/2001 | Brunel ...................... 604/110 |
| 7,094,224 | B2 | * | 8/2006 | Lourenco et al. .......... 604/227 |

FOREIGN PATENT DOCUMENTS

| EP | 0 242 956 | 10/1987 |
| FR | 2 245 382 | 4/1975 |
| FR | 2 799 375 | 4/2001 |
| FR | 2 830 199 | 4/2003 |
| WO | WO 00/69492 | 11/2000 |
| WO | WO 01/49347 A1 * | 7/2001 |

* cited by examiner

*Primary Examiner*—Tatyana Zalukaeva
*Assistant Examiner*—Michael G Bogart
(74) *Attorney, Agent, or Firm*—James R. Williams (57) ABSTRACT

The security assembly is designed to be fitted to a syringe comprising a body provided with one end for connection to an injection needle and one end for inserting a piston. The security assembly comprises a member for fitting to the body of the syringe so as to be constrained axially relative to the body, and a security cap for covering the injection end of the body, the cap being provided with a proximal portion for connection to the fitted member and a distal portion for releasing the injection end and connected to the connection portion by frangible means. The fitted member forms a member that is designed to retain the piston inside the body.

23 Claims, 8 Drawing Sheets

SECURITY ASSEMBLY FOR FITTING TO A SYRINGE, AND A SYRINGE ASSEMBLY

The present invention relates to a security assembly for fitting to a syringe, and to a syringe assembly.

BACKGROUND OF THE INVENTION

Certain medical products are packaged directly in a standard syringe body (prefilled syringe), generally made of glass, and closed by a piston which is connected to a plunger for actuating the piston.

The body of a syringe is generally provided with an end for connection to an injection needle, referred to as the injection end, and an end for inserting the piston. It is thus possible to access the substance contained in the syringe via each of said ends, e.g. either by withdrawing the piston from the body of the syringe, or else by expelling or sucking in substance through the needle. It is also possible to access the substance contained in the syringe by means of an injection needle that is pushed through the piston, which is generally made of elastomer, after the plunger has been removed.

A security assembly is already known in the state of the art, in particular from FR 2 799 375 A1 (FR 9912500), for fitting to a syringe comprising a body provided with one end for connection to an injection needle, referred to as the injection end, and one end for inserting a piston, the security assembly being of the type comprising:

a member for fitting onto the body of the syringe in such a manner as to be constrained axially relative to the body; and
  a security cap for covering the injection end of the body, the cap having a proximal portion for connection to the fitted member, and a distal portion for releasing the injection end and connected to the connection portion by frangible means.

After engaging the proximal portion of the security cap on the body of the syringe, the injection end of the syringe body can be disengaged only by rupturing the frangible means. Thus, fraudulent access to the substance contained in the syringe via the injection end of the body of said syringe is revealed by the frangible means being ruptured.

A member for retaining the piston inside the body of the syringe is also known from the state of the art, in particular from DE 29 45 869 A1, said member serving in particular to prevent the piston being withdrawn in untimely or fraudulent manner.

OBJECTS AND SUMMARY OF THE INVENTION

A particular object of the invention is to reveal and/or avoid fraudulent access to the substance contained in the syringe, in particular when the syringe is for putting on sale, and to do so by using means that are simple and effective.

To this end, the invention provides a security assembly for fitting to a syringe of the above-specified type, wherein the fitted member forms a member that is designed to retain the piston inside the body.

Thus, the security assembly of the invention serves both to prevent access to the injection end of the syringe body (whether or not it is fitted with a needle) until after the frangible means have been ruptured (so that fraudulent access to the substance contained in the syringe via the injection end of the body of said syringe is revealed by said rupture of the frangible means), and also to prevent untimely or fraudulent withdrawal of the piston and/or the plunger from the syringe.

Said security assembly may optionally have other characteristics as follows:

the connection portion of the security cap forms means for retaining the fitted member radially on the body of the syringe;
  the fitted member comprises at least one annular skirt sector referred to as a centering sector for co-operating with a complementary surface delimiting the body of the syringe for positioning the fitted member radially relative to the body of the syringe;
  the security cap is connected to the fitted member by complementary snap-fastening means carried by the connection portion of the security cap and by the fitted member, the complementary snap-fastening means being engageable one in the other in irreversible manner;
  the complementary snap-fastening means comprise complementary locking shoulders formed respectively on a substantially annular end of the connection portion of the security cap, and on at least one annular skirt sector secured to the fitted member, and referred to as the snap-fastening sector;
  the centering sector is radially inside the snap-fastening sector, the substantially annular end of the connection portion of the security cap being radially interposed between the centering sector and the snap-fastening sector;
  the locking shoulder formed on the snap-fastening sector is adjacent to circumferential slots formed in the snap-fastening sector;
  the security assembly is designed to be fitted to a syringe comprising a body provided with one end for inserting a piston, said end being defined by a collar, and the fitted member comprises proximal and distal plates for gripping axially on either side of the collar to prevent the fitted member from moving axially relative to the body of the syringe, the proximal plate forming a flange for retaining the piston inside the body;
  the distal plate carries the centering sector;
  the distal plate carries the snap-fastening means for co-operating with the complementary snap-fastening means carried by the connection portion of the security cap;
  the distal plate includes an engagement opening for engaging around the body of the syringe, said engagement opening out in a direction that is substantially parallel to the plates, the outline of the distal plate that defines said engagement opening preferably being U-shaped;
  the security assembly is designed to be fitted to a syringe comprising a body provided with a piston, and the security assembly comprises a plunger-forming rod designed to be connected to the piston, and the proximal plate includes a clearance opening for allowing the plunger to move axially, said clearance opening preferably opening out in a direction that is substantially parallel to the plates, the outline of the proximal plate that delimits the clearance opening forming the flange for retaining the piston and preferably being U-shaped;
  the plunger has a distal end inside the body provided with a disk forming protection against the piston being pierced and/or an abutment for co-operating with the proximal flange-forming plate to retain the piston and the distal end of the plunger inside the body;
  the fitted member includes means for preventing turning movements, which means are designed to co-operate with complementary means of the collar of the body of the syringe, said means for preventing turning movements being preferably provided with flats formed in the fitted member so as to extend axially between the two plates;

the fitted member is provided with means against which the fingers of a user can bear, said means preferably comprising two radial finger tabs that are substantially diametrically opposite;

the security cap is generally in the form of a body of revolution, the frangible means comprising an annular slot between the two portions of the security cap, said slot being interrupted by frangible bridges connecting together the two portions of the security cap;

the release portion and the connection portion of the security cap are provided with complementary connection means suitable for co-operating mutually after the frangible means have been ruptured;

the complementary connection means comprise mutually engageable complementary snap-fastening means provided with complementary locking shoulders and with complementary end of engagement stroke abutments formed respectively on the release portion and on the connection portion of the security cap;

the complementary end of stroke abutments are delimited respectively by an outward projection, e.g. an annular projection, formed on one of the portions of the security cap, and by an edge of the other portion of the security cap delimiting the annular slot;

the security cap is made of a transparent material, in particular to give visual access to a label carried by the syringe;

the release portion of the security cap is designed to form a protective cap for the injection needle; and the release portion of the security cap is designed to be connected to a protective cap for the injection needle.

The invention also provides a syringe assembly of the type comprising a syringe having a body provided with one end for connection to an injection needle, referred to as the injection end, and one end for inserting a piston, the assembly further comprising a security assembly as defined above.

BRIEF DESCRIPTION OF THE DRAWINGS

The invention will be better understood on reading the following description given purely by way of example and made with reference to the accompanying drawings, in which.

MORE DETAILED DESCRIPTION

Figure 1:
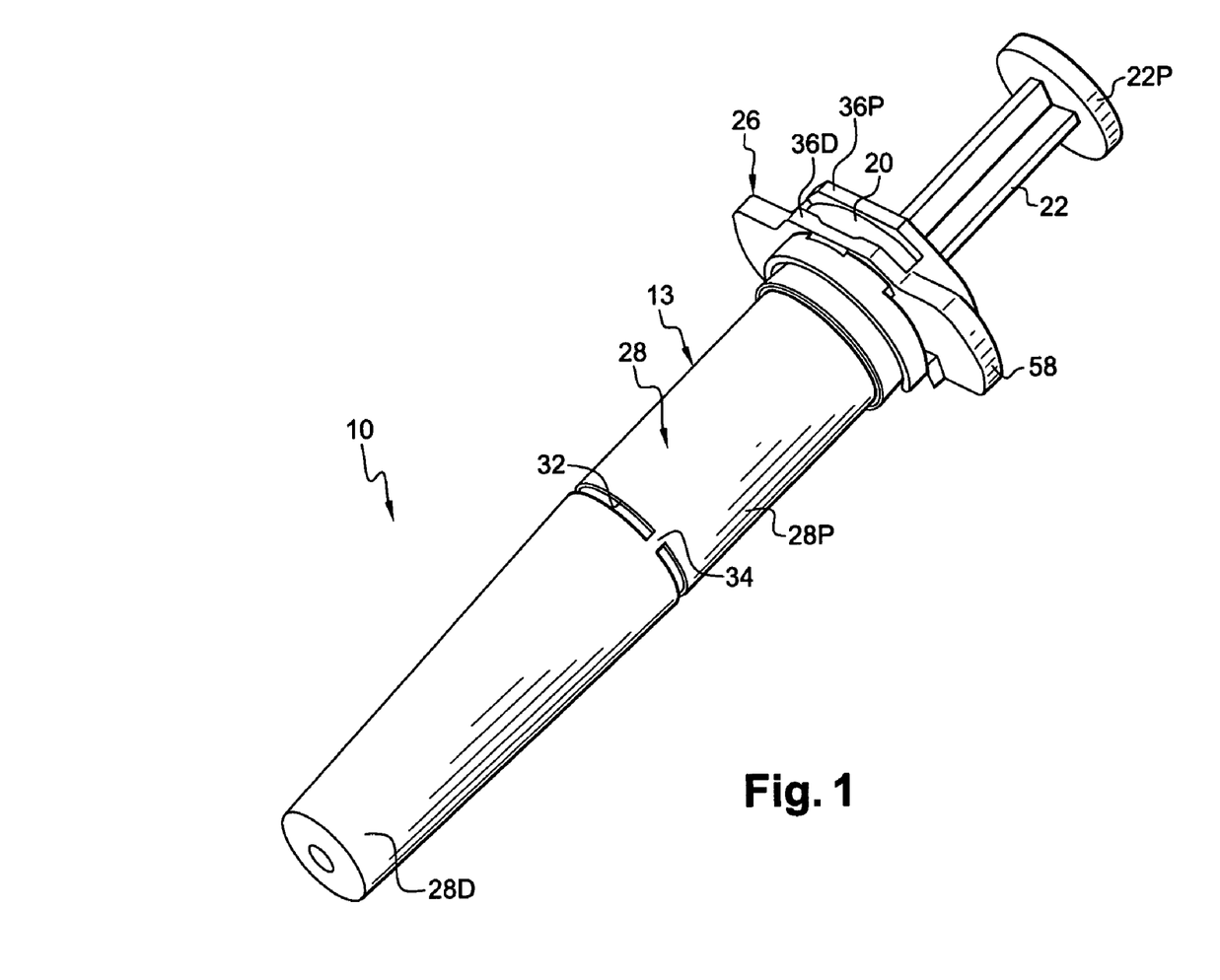
FIG. 1 is a perspective view of a-syringe assembly in a first embodiment of the invention.
Figure 2:
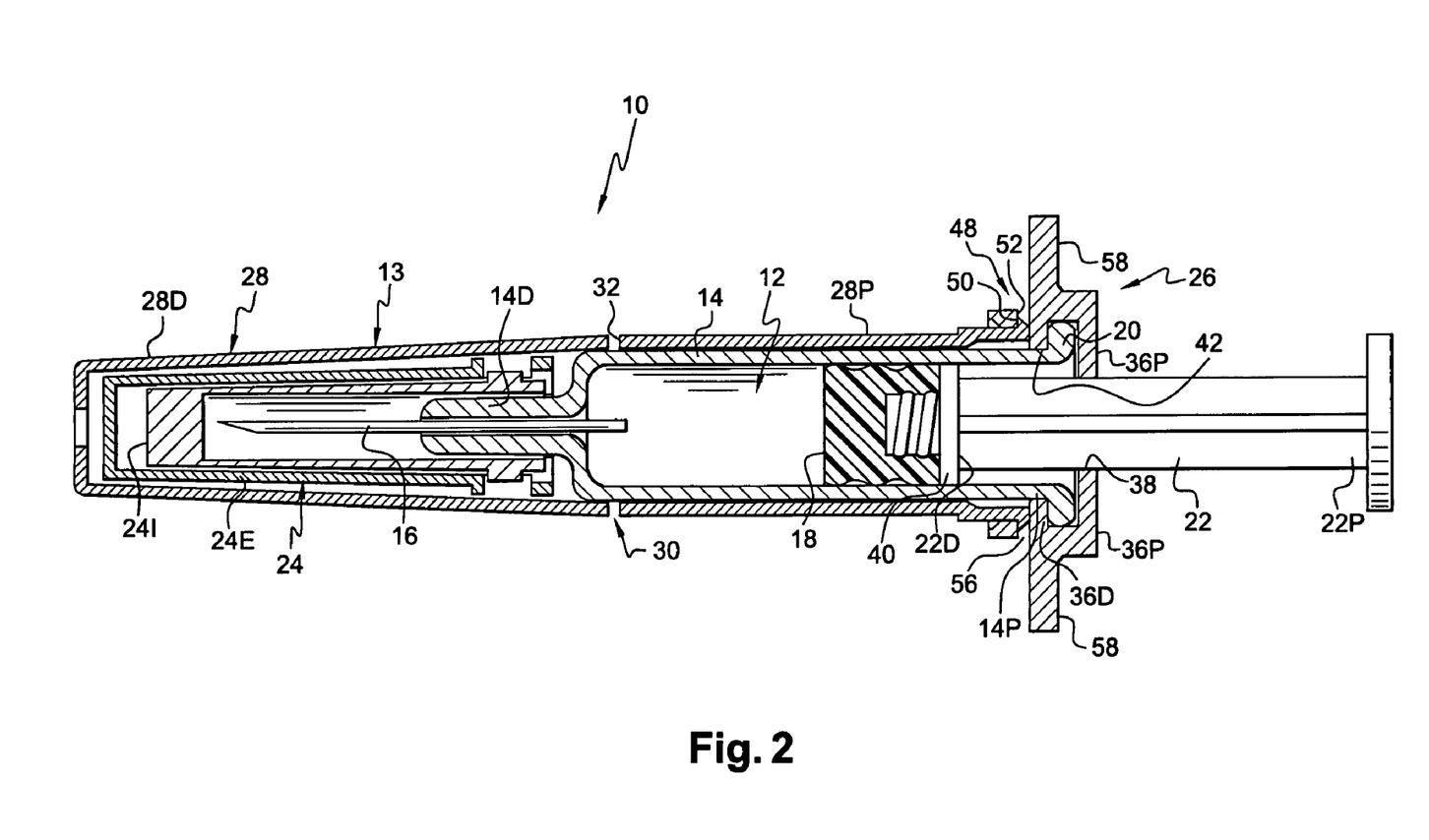
FIG. 2 is an axial section view of the syringe assembly shown in FIG. 1.

FIGS. 1 and 2 show a syringe assembly in a first embodiment of the invention, given overall reference 10.

The syringe assembly 10 comprises a syringe 12 for injecting a liquid, in particular of the medical type, and fitted with a security assembly 13 of the invention.

Below, the term proximal is used to designate an element of the syringe assembly or of the security assembly that is axially close to the hand of a user, and the term distal is used to designate an element of said syringe assembly or security assembly that is remote from the hand of the user.

Figure 3:
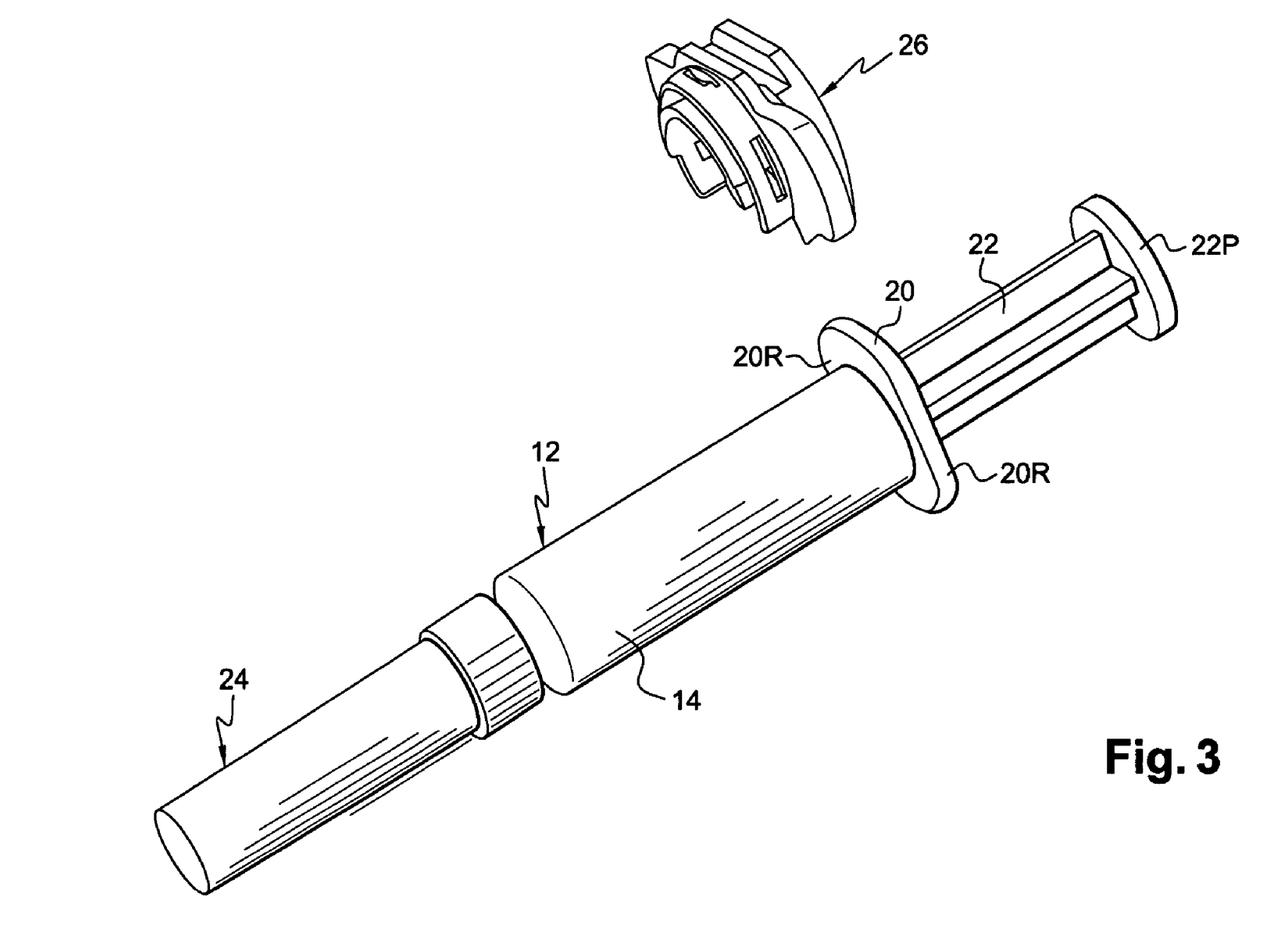
FIGS. 3 to 5 are partially exploded perspective views showing at least a portion of the syringe assembly shown in FIG. 1 in various configurations during assembly or use.

In conventional manner, the syringe 12 shown in particular in FIGS. 2 and 3 comprises a tubular body 14, e.g. made of glass. The body 14 is provided with a distal end 14D for connection to an injection needle 16. This end 14D is referred to below as the injection end. The body 14 is also provided with a proximal end 14P that is open and that allows a piston 18 to be inserted into the body 14. This piston 18 is of conventional type, and can be made of elastomer, for example.

It should be observed that the insertion end 14P is defined by a collar 20. In the example described, the collar 20 is delimited by a circular outline that is interrupted by two substantially rectilinear portions 20R that are diametrically opposite and that can be seen in particular in FIG. 3. In a variant, the collar may be delimited by a circular outline that is not interrupted.

The security assembly 13 comprises a security plunger 22 having a distal end 22D inside the body 14 and connected to the piston 18, e.g. by screw-fastening, and a proximal end 22P outside the body 14, forming the driving end of the plunger 22.

The injection end 14D of the body and the needle 16 are covered by a conventional protective cap 24 which is provided in the example described with an outer casing 24E and an inner casing 24I, e.g. made of elastomer.

The security assembly 13 also comprises a member 26 fitted on the body 14 and a security cap 28 covering the protective cap 26, the needle 16, and the injection end 14D of the syringe body, by surrounding them.

The security cap 28 is provided with a proximal portion 28P for connection to the body 14 of the syringe via the fitted member 26, and with a distal end 28D for releasing the injection end 14D of the syringe body. The connection portion 28P is connected to the release portion 28D by frangible means 30.

It should be observed that the syringe 12 and the security cap 28 are generally in the form of bodies of revolution.

The frangible means 30 of the security cap 28 comprise, for example, an annular slot 32 between the two portions 28D and 28P of the security cap. The slot 32 is interrupted by frangible bridges 34 interconnecting the two portions 28D and 28P of the security cap.

The security cap 28 is preferably made of a transparent material, e.g. a plastics material, so as to give visual access to a label carried by the syringe 12, e.g. by the protective cap 24.

The axial position of the frangible means 30 on the security cap 28 may vary depending on requirements. When the syringe 12 carries a label that is to be unstuck or peeled off, the frangible means 30 are preferably positioned on the security cap 28 so that after the frangible means have been ruptured, it is possible to access the label to unstick it or peel it off.

In a first variant, the protective cap 24 may be omitted, with the release portion 28D of the security cap 28 then forming a protective cap for the injection needle 16.

In a second variant, the release portion 28D of the security cap may be connected to the protective cap 28 so that separating the release portion 28D from the connection portion 28P of the security cap causes the protective cap 24 to be separated from the injection end 14D of the body of the syringe.

Figure 6:
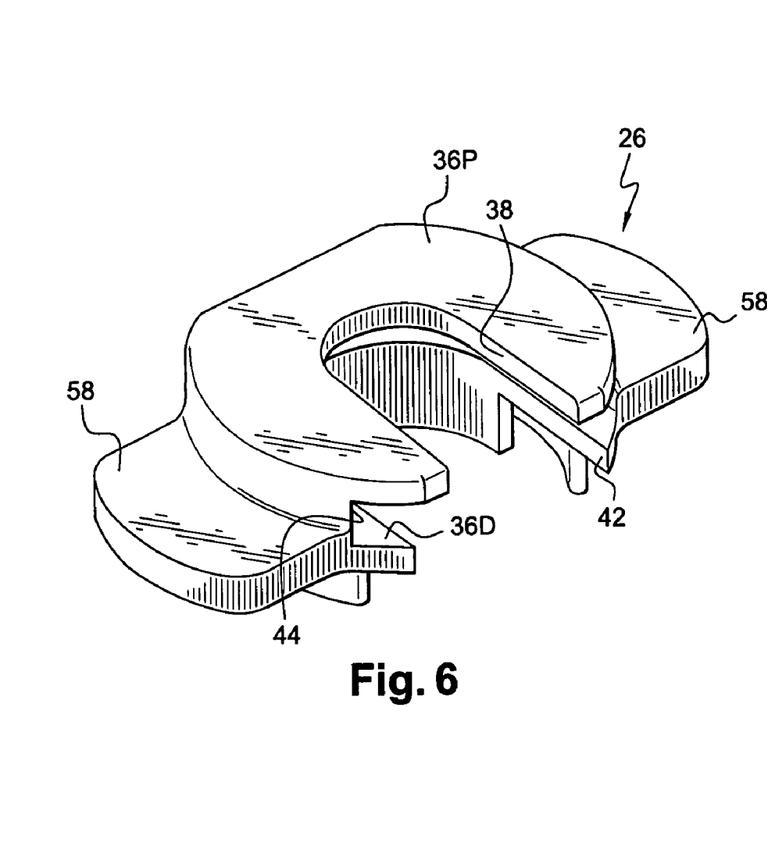
FIGS. 6 and 7 are perspective views from two different points of view showing a member for fitting to the body of the syringe of the syringe assembly shown in FIG. 1.
Figure 7:
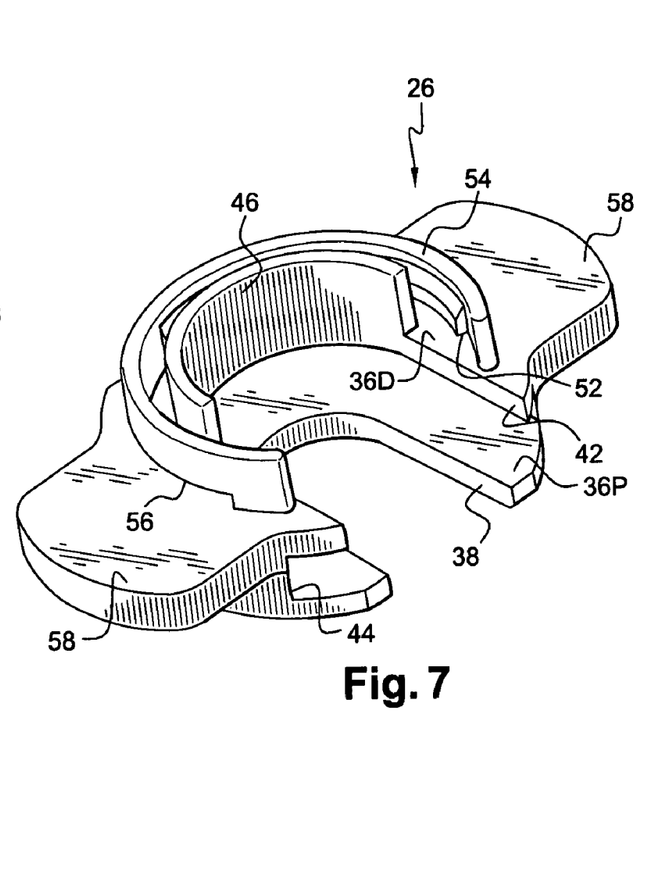

With reference firstly to FIGS. 1 and 2 and secondly to FIGS. 6 and 7 in which the fitted member 26 is shown in detail, it can be seen that this fitted member 26 comprises proximal and distal plates 36P and 36D for receiving the collar 20 between them so as to secure the fitted member 26 axially on the body 14 of the syringe.

The fitted member 26 forms a member that is designed to retain the piston 18 and the distal end 22D of the plunger inside the body 14 of the syringe. The proximal plate 36P forms a flange for retaining the piston 18 inside the body 14.

It should be observed more particularly that the proximal plate 36P has an opening 38 for allowing the plunger 22 to move axially. The outline of the proximal plate 36P delimiting this clearance opening 38 forms the flange for retaining the piston 18. The clearance opening 38 preferably opens out in a direction that is substantially parallel to the plates 36P and 36D, i.e. in a direction that is substantially perpendicular to the axis of the syringe 12. The outline of the proximal plate 36P delimiting this opening 38 is preferably U-shaped so as to present edges that are substantially rectilinear and parallel, which edges are spaced apart by a distance that is suitable for allowing the proximal plate 36P to move transversely relative to the plunger 22.

It should be observed that the inside end 22D of the plunger is provided with a disk 40 constituting an abutment for retaining the piston 18 and designed to co-operate with the flange-forming proximal plate 36P. In the example shown, the disk 40 is axially adjacent to the piston 18. In addition, the disk 40 forms protection for preventing the piston 18 being pierced.

The distal plate 36D has an opening 42 to enable the distal plate 36D to be engaged around the body 14 of the syringe. This engagement opening 42 opens out in a direction that is substantially parallel to the plates 36D and 36P, i.e. in a direction that is substantially perpendicular to the axis of the syringe 12. The outline of the distal plate 36D defining the engagement opening 42 is preferably U-shaped so as to present edges that are substantially rectilinear and parallel, and that are spaced apart by a distance that is suitable for allowing the distal plate 36D to be engaged transversely on the body 14 of the syringe.

The fitted member 26 preferably includes a pair of diametrically opposite flats 44 arranged on said fitted member 26 in such a manner as to extend axially between the two plates 36P and 36D. These flats 44 can form means for preventing the fitted member 26 from turning relative to the body 14 of the syringe by co-operating with the rectilinear edges 20R of the collar forming complementary means for preventing turning.

Figure 4:
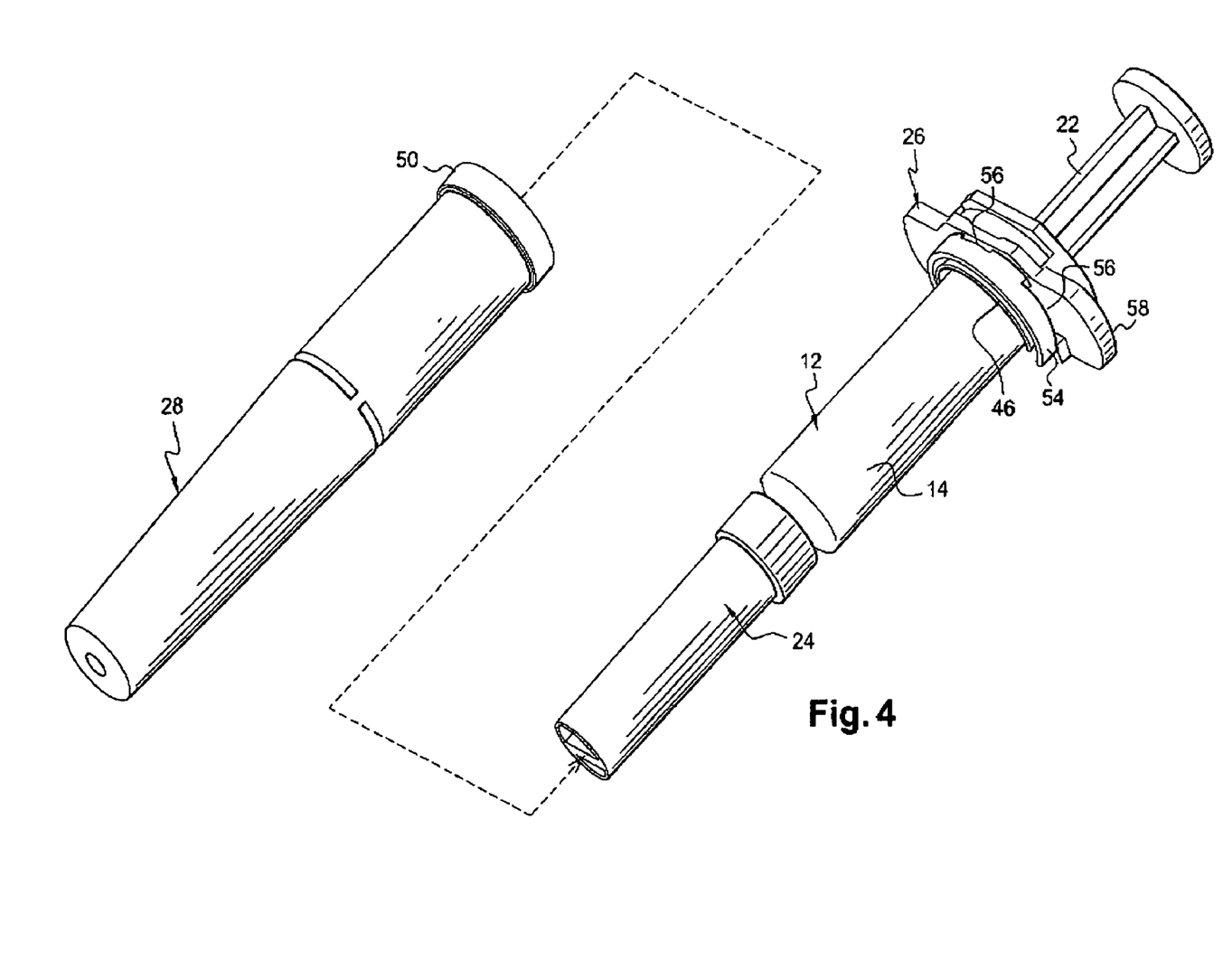

With reference in particular to FIGS. 4, 6, and 7, it can be seen that the distal plate 36D includes at least one sector 46 of an annular skirt referred to as a centering sector which is designed to co-operate with a complementary surface defining the body 14 of the syringe so as to position the fitted member 26 radially to the body 14. In the example shown, the centering sector 46, which is molded integrally with the distal plate 36D, extends over substantially 180° and co-operates with the outside surface of the body 14 of the syringe.

The security cap 28 is designed to be connected to the fitted member 26. After being connected to the fitted member 26, the security cap 28 extends around the body 14 of the syringe, being substantially coaxial about the body 14. Thus, the security cap 28, and more particularly the connection portion 28P thereof, forms means for retaining the fitted member 26 radially on the body 14 of the syringe.

The security cap 28 is preferably connected to the fitted member 26 by complementary snap-fastening means 48 carried by the connection portion 28P of the security cap and by the fitted member 26. These complementary snap-fastening means 48 are irreversibly engageable one in the other, i.e. if the snap-fastening means 28 should ever be disengaged, that will leave a visible trace.

In the example shown in the figures, the complementary snap-fastening means 48 comprise complementary locking shoulders 50 and 52 formed respectively on a substantially annular end of the connection portion 28P of the security cap (see in particular FIGS. 2 and 4), and on at least a sector 54 of the annular skirt that is integrally molded with the distal plate 36D of the fitted member (see in particular FIGS. 2 and 7). The sector 54 is referred to below as the snap-fastening sector.

In the example shown, the centering sector 46 extends over more than 180°.

With reference in particular to FIGS. 1 and 7, it can be seen that the locking shoulder 52 formed on the snap-fastening sector 54 is axially adjacent to circumferential slots 56 formed in the snap-fastening sector 54. These slots 56 facilitate snap-fastening of the complementary means 48.

With reference in particular to FIGS. 4 and 7, it should also be observed that the centering sector 46 is radially inside the snap-fastening sector 54. After the complementary means 48 have been snap-fastened, the substantially annular end of the connection portion 28P of the security cap is interposed radially between the centering sector 46 and the snap-fastening sector 54.

The fitted member 26 is preferably provided with means against which the fingers of a user can bear, for example means comprising two radial finger tabs 58 that are substantially diametrically opposite.

It should be observed that the security assembly 13 can be sold independently of the syringe 12 in the form of a kit comprising the security plunger 22, the fitted member 26 and the security cap 28, these various elements of the kit being suitable for mounting on the syringe 12, optionally a prefilled syringe, comprising the body 14 and the piston 18.

The security assembly 13 of the invention is very simple to mount on the syringe 12.

Initially, the plunger 22 is connected to the piston 18 so as to obtain the assembly shown in FIG. 3, in which the protective cap 24 is engaged on the injection end 14D of the body of the syringe.

Mounting of the security assembly 13 on the syringe 12 is then continued by engaging the fitted member 26 onto the collar 20 of the body 14 of the syringe. This engagement is performed by moving the member 26 relative to the body 14 of the syringe in a direction that is substantially perpendicular to the axis of the syringe 12, as is made possible by the U-shaped openings 38 and 42 formed in the proximal and distal plates 36P and 36D of the fitted member.

In the configuration of FIG. 4, the fitted member 26 is prevented from moving axially relative to the body 14 of the syringe, but it is not retained radially on the body 14. It should be observed that the fitted member 26 can be mounted on the collar 20 in the presence of the plunger 22 of said syringe 12.

Once the fitted member 26 is connected to the body 14 of the syringe as shown in FIG. 4, the security cap 28 is snap-fastened to the fitted member 26 in such a manner that the cap 28 covers the body 14 of the syringe and also covers the cap 24 for protecting the needle 16, as shown in FIG. 1.

After the security cap 28 has been snap-fastened to the fitted member 26, the fitted member is prevented from moving radially relative to the body 14 of the syringe.

Figure 5:
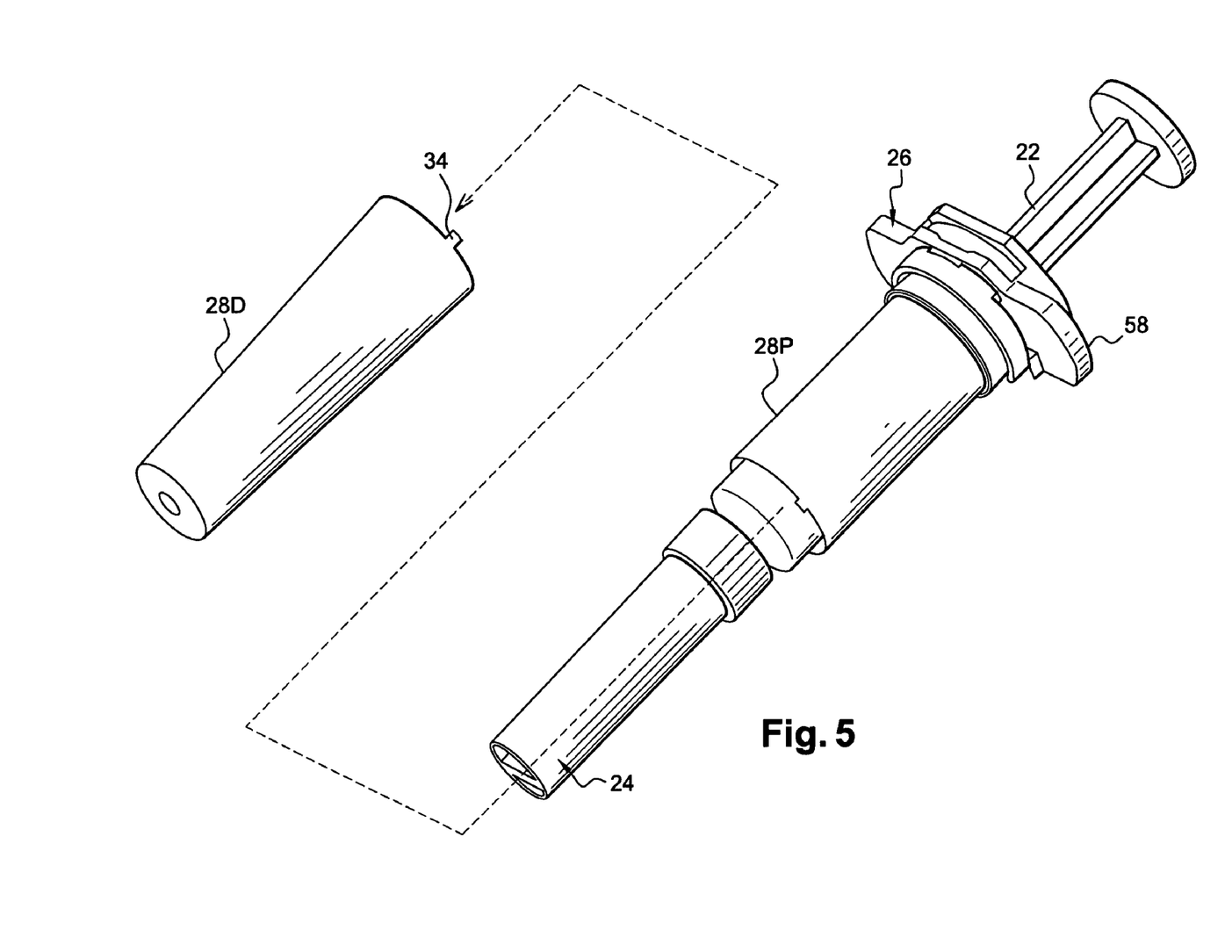

In order to access the needle 16 of the syringe, a user acts on the release end 28D of the security cap so as to rupture the frangible bridges 34 and separate the release portion 28D from the connection portion 28P which remains connected to the fitted member 26, as shown in FIG. 5.

After the release portion 28D of the security cap has been withdrawn, the user can access the protective cap 24 and remove it in the normal manner from the syringe so as to be able to make use of the syringe under the usual conditions.

Since the needle 16 of the syringe can be accessed only after rupturing the frangible bridges 34 and separating the release portion 28D of the security cap from the connection portion 28P of said cap, it is easy to detect any dishonest access to the needle 16.

Furthermore, the flange-forming fitted member 26 prevents any untimely or dishonest withdrawal of the piston 18 from the body 14 of the syringe.

Where appropriate, in order to be able to detect fraudulent replacement of an element of the security assembly 13, at least one element of the security assembly 13, for example the security cap 28 or the fitted member 26, may include a chemical element or a marking that is invisible to the naked eye but that can be detected using appropriate means such as an ultraviolet or infrared spectrometer or indeed illumination using suitable radiation, in particular ultraviolet radiation.

Optionally, a frangible zone may be provided on the plunger 22 and/or the fitted member 26 in order to cause one or the other of these members to rupture in the event of an attempt at forcibly withdrawing the piston 18 from the body 14 of the syringe.

Figure 8:
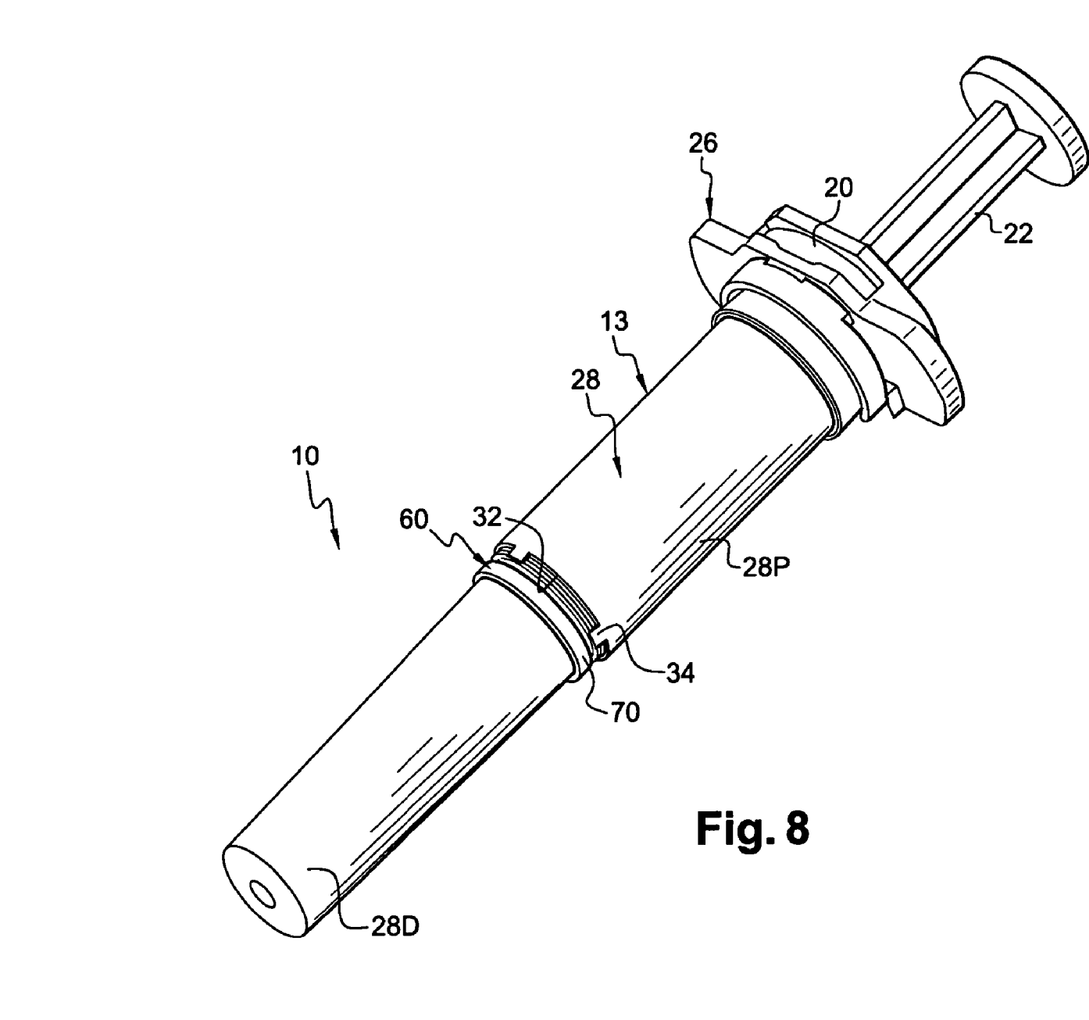
FIG. 8 is a view similar to FIG. 1 showing a syringe assembly in a second embodiment of the invention.
Figure 9:
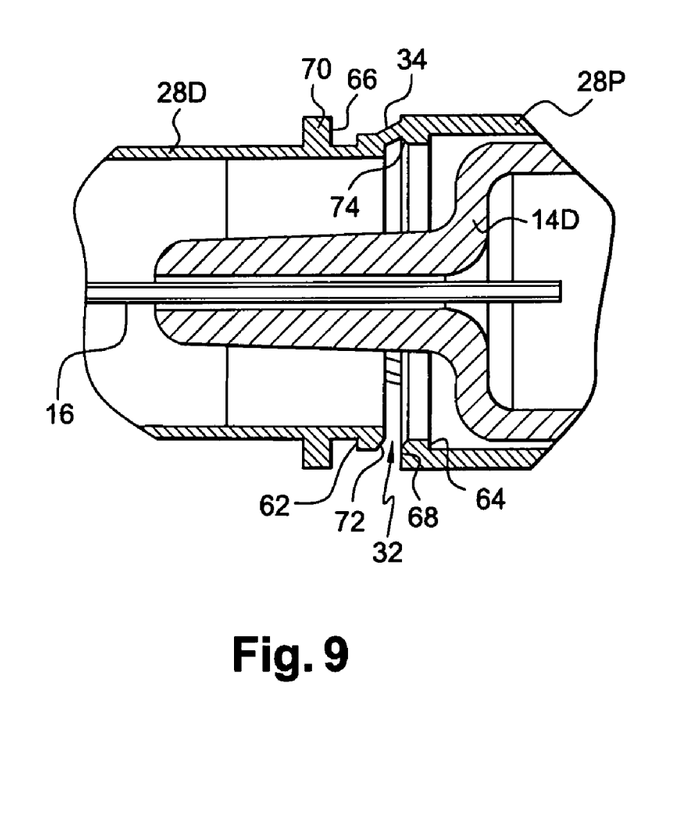
FIGS. 9 and 10 are fragmentary axial section views of the syringe assembly shown in FIG. 8 showing the security cap before and after first use of the syringe.
Figure 10:
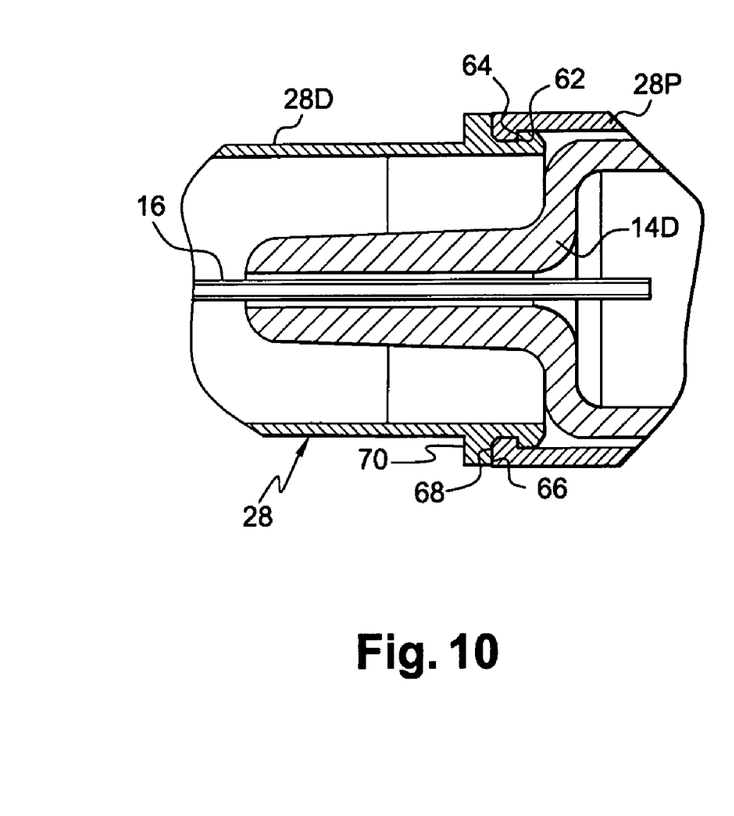

FIGS. 8 to 10 show a syringe assembly in a second embodiment of the invention. In these figures, elements that are analogous to those shown in FIGS. 1 to 7 are designated by identical references.

For reasons of clarity, the protective cap 24 is not shown in FIGS. 9 and 10.

In this embodiment, the release portion 28D and the connection portion 28P of the security cap 28 are provided with complementary connection means suitable for co-operating mutually after the frangible means 30 have been ruptured so that after first use of the syringe under the usual conditions, it is possible to isolate the injection end 14D and the needle 16 of the syringe from the outside.

Preferably, as can be seen in particular in FIGS. 9 and 10, the complementary connection means comprise mutually engageable complementary snap-fastening means 60 provided with complementary locking shoulders 62 and 64 and complementary end-of-engagement stroke abutments 66, 68 provided on the release portion 28D and on the connection portion 28P respectively of the security cap 28.

The complementary end-of-stroke abutments 66 and 68 are defined respectively by an outward projection 70, e.g. of annular shape, formed on one of the portions of the security cap 28, specifically the release portion 28D in the example shown, and an edge on the other portion of the cap 28, specifically the connection portion 28P in the example shown, defining the annular slot 32 prior to rupture of the frangible bridges 34 (see FIG. 9).

It should be observed that prior to being ruptured, the frangible bridges 34 extend substantially between engagement ramps 72, 74 of the complementary snap-fastening means 60.

As in the first embodiment of the invention, in order to access the needle 16 of the syringe, a user acts on the release end 28D of the security cap so as to rupture the frangible bridges 34 and separate said release portion 28D from the connection portion 28P which remains connected to the fitted member 26.

After the release portion 28D of the security cap has been withdrawn, the user can use the syringe under the usual conditions.

After said use, the user isolates the injection end 14D and the needle 16 from the outside by snap-fastening the release portion 28D onto the connection portion 28P of the security cap, as shown in FIG. 10. The complementary snap-fastening means 60 are preferably mutually engageable in irreversible manner.

The invention is not limited to the embodiments described above.

In particular, the fitted member 26 intended specifically for retaining the piston 18 in the body of the syringe, may be of a structure that is different from that described above.

Furthermore, the radial positioning of the fitted member relative to the body of the syringe may be received by means carried by the security cap rather than by the centering sector carried by the fitted member.

What is claimed is:

1. A security assembly for fitting to a syringe comprising a body provided with one end for connection to an injection needle, referred to as the injection end, and one end for inserting a piston connected to a plunger, the security assembly being of the type comprising:
   a fitted member for fitting to the body of the syringe in so as to be constrained axially relative to the body; and
   a security cap for covering the injection end of the body, the cap being provided with a proximal portion for connection to the fitted member and a distal portion for releasing the injection end and connected to the connection portion by frangible means;
   wherein the plunger goes through the fitted member the fitted member comprising a flange that is designed to prevent the withdrawal of the piston from inside the body.

2. A security assembly according to claim 1, wherein the proximal portion of the security cap forms means for retaining the fitted member radially on the body of the syringe.

3. A security assembly according to claim 1, wherein the fitted member comprises at least one annular skirt sector referred to as a centering sector for co-operating with a complementary surface delimiting the body of the syringe for positioning the fitted member radially relative to the body of the syringe.

4. A security assembly according to claim 1, wherein the security cap is connected to the fitted member by complementary snap-fastening means carried by the proximal portion of the security cap and by the fitted member, the complementary snap-fastening means being engageable one in the other in irreversible manner.

5. A security assembly according to claim 4, wherein the fitted member comprises at least one annular skirt sector, and the complementary snap-fastening means comprise complementary locking shoulders formed respectively on a substantially annular end of the proximal portion of the security cap, and on at least one annular skirt sector and referred to as die snap-fastening sector.

6. A security assembly according to claim 5, wherein the fitted member comprises at least one annular skirt sector referred to as a centering sector for co-operating with a complementary surface delimiting the body of the syringe for positioning the fitted member radially relative to the body of the syringe, and wherein the centering sector is radially inside the snap-fastening sector, the substantially annular end of the proximal portion of the security cap being radially interposed between the centering sector and the snap-fastening sector.

7. A security assembly according to claim 5, wherein the locking shoulder formed on the snap-fastening sector is adjacent to circumferential slots formed in the snap-fastening sector.

8. A security assembly according to claim 1, for fitting to a syringe comprising a body provided with one end for inserting a piston, said end being defined by a collar, wherein the lined member comprises proximal and distal plates for gripping axially on either side of the collar to prevent the fitted member from moving axially relative to the body of the syringe, the proximal plate forming a flange for retaining the piston inside the body.

9. A security assembly according to claim 3, for fitting to a syringe comprising a body provided with one end for inserting a piston, said end being defined by a collar, wherein the fitted member comprises proximal and distal plates for disposing axially on either side of the collar to prevent the fitted member from moving axially relative to the body of the syringe, the proximal plate forming a flange for retaining the piston inside the body, and wherein the distal plate carries the centering sector.

10. A security assembly according to claim 9, wherein the security cap is connected to the fitted member by complementary snap-fastening means carried by the proximal portion of the security cap and by the fitted member, the complementary snap-fastening means being engageable one in the other in irreversible manner, and wherein the distal plate carries the snap-fastening means for co-operating with the complementary snap-fastening means carried by the proximal portion of the security cap.

11. A security assembly according to claim 8, wherein the distal plate includes an engagement opening for engaging wound the body of the syringe, said engagement opening opening out in a direction that is substantially parallel to the plates, the outline of the distal plate that defines said engagement opening preferably being U-shaped.

12. A security assembly according to claim 8, for fitting to a syringe comprising a body provided with a piston, the assembly comprising a plunger-forming rod designed to be connected to the piston, and wherein the proximal plate includes a clearance opening for allowing the plunger to move axially, said clearance opening preferably opening out in a direction that is substantially parallel to the plates, the outline of the proximal plate tat delimits the clearance opening forming the flange for retaining the piston and preferably being U-shaped.

13. A security assembly according to claim 12, wherein the plunger has a distal end inside the body provided with a disk forming protection against the piston being pierced and/or an abutment for co-operating with the proximal flange-forming plate to retain the piston and the distal end of the plunger inside the body.

14. A security assembly according to claim 8, wherein the fitted member includes means for preventing turning movements, which means are designed to cooperate with complementary means of the collar of the body of the syringe, said means for preventing turning movements being preferably provided with flats formed in the fitted member so as to extend axially between the two plates.

15. A security assembly according to claim 1, wherein the fitted member is provided with means against which the fingers of a user can bear, said means preferably comprising two radial finger tabs that are substantially diametrically opposite.

16. A security assembly according to claim 1, wherein the security cap is generally in the form of a body of revolution, the frangible means comprising an annular slot between the two portions of the security cap, said slot being interrupted by frangible bridges connecting together the two portions of the security cap.

17. A security assembly according to claim 1, wherein the release portion and the connection portion of the security cap are provided with complementary connection means suitable for co-operating mutually after the frangible means have been ruptured.

18. A security assembly according to claim 17, wherein the complementary connection means comprise mutually engageable complementary snap-fastening means provided with complementary locking shoulders and with complementary end of engagement stroke abutments formed respectively on the release portion and on the connection portion of the security cap.

19. A security assembly according to claim 18, wherein the security cap is generally in the form of a body of revolution, the frangible means comprising an annular slot between the two portions of the security cap, said slot being interrupted by frangible bridges connecting together the two portions of the security cap and wherein the complementary end of stroke abutments are delimited respectively by an outward projection, e.g. an annular projection, formed on one of the portions of the security cap, and by an edge of the other portion of the security cap delimiting the annular slot.

20. A security assembly according to claim 1, wherein the security cap is made of a transparent material, in particular to give visual access to a label carried by the syringe.

21. A security assembly according to claim 1, wherein the distal portion of the security cap is designed to form a protective cap for the injection needle.

22. A security assembly according to claim 1, wherein the distal portion of the security cap is designed to be connected to a Protective cap for the injection needle.

23. A syringe assembly of the type comprising a syringe having a body provided with one end for connection to an injection needle, referred to as the injection end, and one end for inserting a piston connected to a plunger, die assembly further comprising a security assembly fitted to the syringe, the security assembly comprising:

a fitted member for fitting to the body of the syringe in so as to be constrained axially relative to the body; and a security cap for covering the injection end of the body, the cap being provided with a proximal portion for connection to the fitted member and a distal portion for releasing the injection end and connected to the proximal portion by frangible means;

wherein the plunger goes through the fitted member the fitted member comprising a flange that is designed to prevent the withdrawal of the piston from inside the body.

* * * * *